United States Patent [19]

Franzmann et al.

[11] 4,182,904

[45] Jan. 8, 1980

[54] METHOD OF RACEMIZING OPTICALLY ACTIVE N-ACYL AMINO ACIDS IN AQUEOUS SOLUTION

[75] Inventors: Giselher Franzmann, Witten; Hans-Leo Hulsmann, Wetter, both of Fed. Rep. of Germany

[73] Assignee: Dynamit Nobel Aktiengesellschaft, Troisdorf, Fed. Rep. of Germany

[21] Appl. No.: 935,835

[22] Filed: Aug. 22, 1978

[30] Foreign Application Priority Data

Sep. 8, 1977 [DE] Fed. Rep. of Germany ....... 2740380

[51] Int. Cl.$^2$ ............................................. C07B 20/00
[52] U.S. Cl. ..................................... 562/401; 562/450
[58] Field of Search .............. 562/401, 443, 444, 445, 562/450, 553, 556, 559, 562, 570, 573

[56] References Cited

U.S. PATENT DOCUMENTS

| 2,071,327 | 2/1937 | Bley | 562/401 |
| 3,737,454 | 6/1973 | Chibata et al. | 562/401 |
| 3,991,077 | 11/1976 | Uzuki et al. | 562/401 X |

OTHER PUBLICATIONS

Chemical Abstracts I, vol. 55, 3449d, (1961).
Chemical Abstracts II, vol. 55, 27105f, (1961).

*Primary Examiner*—James O. Thomas, Jr.
*Assistant Examiner*—Vera C. Clarke
*Attorney, Agent, or Firm*—Sprung, Felfe, Horn, Lynch & Kramer

[57] ABSTRACT

A process has been invented for the racemization of optically active N-acylamino acids in aqueous solution which comprises treating said optically active N-acylamino acids with ketene.

9 Claims, No Drawings

METHOD OF RACEMIZING OPTICALLY ACTIVE N-ACYL AMINO ACIDS IN AQUEOUS SOLUTION

BACKGROUND

The subject matter of the present invention is a simple chemical process for the rapid racemization of optically active N-acylamino acids which are in aqueous solution.

The preparation of L-amino acids corresponding in configuration to the naturally occurring amino acids from synthetic amino acid racemates can be accomplished by selectively deacylating the N-acyl-L isomers by the action of N-acyl-L-amino acid amidohydrolases (called "acylases" for brevity). The aqueous cleavage solutions contain, after the separation of the target product, i.e., the L-amino acid, the enzymatically uncleaved L-acyl-D form. This has to be racemized so that it can be returned to the enzymatic cleavage process and again yield L-amino acids after the asymmetrical hydrolysis of the N-acyl-L content. In this manner it becomes possible to transform all of the racemic amino acid to the desired L form.

The known methods for the racemization of optically active N-acyl amino acids have serious disadvantages. The racemization of optically active N-acyl amino acids in the melt is accompanied by decomposition by high temperatures and long action times. Also, the process would be applicable to the dilute aqueous solutions resulting from the enzymatic cleavage of the N-acyl-L form, only after the difficult separation and refinement of the N-acyl-D compound, if it were possible to avoid thermal decomposition. The racemization of optically active N-acyl amino acids in special organic solvents requires the concentration of the amino acid solution, acidification with mineral acid, extraction with the solvent, and heating in the solvent to more than 160° C., and then the removal of the solvents, and therefore it is too complicated and expensive. The racemization of N-acetyl amino acids in aqueous solutions with acetic anhydride requires long reaction times and large amounts of anhydride and caustic soda solution.

THE INVENTION

It has been found that dextro or levo N-acyl amino acid in aqueous solution can be racemized rapidly and with little expenditure of reagent by means of ketene, only one mole of acetic acid forming from one mole of ketene, whereas one mole of acetic anhydride yields two moles of acetic acid as by-product when used for the racemization. Since ketene is the foreproduct of the large-scale manufacture of acetic anhydride from acetic acid, the direct use of ketene for the racemization constitutes a simpler and particularly economical solution of the problem.

The subject matter of the invention, therefore, is a method for the racemization of optically active N-acyl amino acids in aqueous solution, which is characterized in the fact that an aqueous solution of a metal salt, preferably of an alkali salt of an optically active N-acyl amino acid, is reacted with ketene. The pH of the aqueous solution is generally between 2 and 11.

The N-acyl derivatives to be racemized can originate from natural or synthetic amino acids and are, particularly, α-amino acids. The method is applicable to a number of acyl derivatives of essential and non-essential amino acids, e.g. acylated optical isomers of glycine, alanine, lysine, leucine; isoleucine, serine, phenylglycine, phenylalanine, tyrosine, proline, hydroxy proline, serine, threonine, cysteine, cystine, methionine, tryptophan, aspartic acid, glutamic acid, arginine, lysine, histidine. Amino acids useful in the process of the invention include all amino acids, the amino group of which being directly bond to the "asymmetric carbon atom".

If the amino acid contains an additional acylatable functional group, such as an aliphatic hydroxyl group or an indolyl-NH group, for example, the starting substance can be used in a form in which only the alpha amino group is acylated, but the other functional group is a free, nonacylated group. Then, in a very advantageous manner, by reaction with ketene in the embodiment of the invention, the racemization takes place only on the alpha carbon atom, while the other groups surprisingly are not acylated. Only basic primary or secondary amino groups are acylated.

The acyl group of the optically active N-acyl amino acids is preferably the acetyl group. Examples of other acyl groups are the alkanoyl groups and halo-, particularly chloro-substituted alkanoyl groups, particularly having 1 to 12 carbon atoms, such as the formyl or halo-acetyl groups; or the benzoyl groups, which upon treatment with ketene are partly replaced by the acetyl group.

The racemization of the N-acyl amino acid enantiomers in aqueous solution can be performed in accordance with the present invention at temperatures between 0° C. and the boiling point of the solution in question. For example, N-acetyl D-(or L-)phenylalanine sodium salt, in 30 wt-% solutions, with respect to the acetyl-amino acid, which initially has a pH of 7, can be racemized rapidly (i.e., in from a few minutes to about one hour, depending on the rate of addition of the ketene) at temperatures of 30° to 90° C. with less than one mole of ketene per mole of N-acetyl amino acid with a yield of over 98%; in a 20 wt-% aqueous solution the yield is better than 90%, and at 5° C. with one mole of ketene it will still be approximately 75%; for a complete racemization, at low temperatures of, for example, 5° C., or low concentrations of, for example, less than 20% more ketene is needed.

The progress of the racemization can easily be determined by measuring the optical rotation. Temperatures of 30° to 90° C. are preferred, and temperatures of 50° to 80° C. are greatly preferred.

The concentration of the N-acetyl amino acid in the aqueous solutions can be selected within wide limits, the lower limit being established at about 10 wt-% by the increasing consumption of ketene, and the upper limit at about 50 wt-% by the solubility of the N-acyl amino acid salt. The optimum concentration, however, will also depend on the nature of the amino acid.

Especially desirable are concentrations of 15 to 40 wt-%, preferably of 20 to 35 wt-%.

Suitable salts are alkali salts of the N-acylamino acid enantiomers, such as for example sodium or potassium salts, and other water-soluble salts.

It is advantageous, but not absolutely necessary, to perform the racemization in a solution that is slightly acid before the start. The acidification can be accomplished by the addition of acetic acid or, if desired, other acids. In this manner a greater initial rate is achieved and about 10% less ketene is required. 10 to 30 mole-% of acid is then added, preferably acetic acid. The pH in this advantageous embodiment will then be preferably between 4 and 7.

Preferred for N-acetyl phenylalanine alkali salt are: concentrations of 25 to 35 wt-% with respect to the amino acid, pH values of 4 to 7, the addition of 15 to 25 mole-% acetic acid and temperatures of 50° to 100° C., especially 70° to 80° C.

The solutions of racemates, so prepared, are particularly suitable after the separation of sodium acetate and, optionally, acetic acid, to be used for the further enzymatic cleavage and for obtaining optically active amino acids.

I. Chibata, T. Tosa, T. Sato, T. Mori Methods in Enzymology Vol. XLIV, p. 746 ff Academic Press New York, 1976

EXAMPLES

The following examples are illustrative but not limitative of the invention.

The ketene that was used was taken from ketene generators which delivered between 0.4 and 1.5 moles of ketene per hour. Different reaction times resulting from this have no effect on the consumption of ketene in the racemization of the N-acetyl amino acids, measured in moles of ketene per mole of N-acetyl amino acid.

EXAMPLE 1

Ketene is introduced at 5° C. into an aqueous solution of one mole of N-acetyl-L-phenylalanine sodium salt, pH 7, in which the N-acetyl-L-phenylalanine content is 20 wt-%. After the consumption of 1.0 mole of ketene, 73% of the N-acetyl-L-phenylalanine is racemized; after the consumption of 1.25 moles of ketene, 80% is racemized.

EXAMPLE 2

Ketene is introduced into an identical solution as that of Example 1 at 30° C. After the consumption of 1.2±0.12 moles of ketene, 90% of the N-acetyl-phenylalanine is racemized.

EXAMPLE 3

Ketene is introduced into an identical solution as that of Example 1 at 50° C. After the consumption of 1.05±0.1 mole of ketene, 90% of the N-acetyl L-phenylalanine is racemized.

EXAMPLE 4

Ketene is introduced into an identical solution at 70° C. as that of Example 1. After the consumption of 1.0±0.1 mole of ketene, 90% of the N-acetyl L-phenylalanine is racemized.

EXAMPLE 5

The process of Example 4 is carried out but at 90° C. After the consumption of 1.0 mole of ketene, 90% of the N-acetyl L-phenylalanine is racemized, and after the consumption of 1.18 mole of ketene, 95% of said N-acetyl L-phenylalanine is racemized.

EXAMPLE 6

The process of Example 4 is carried out, but using N-acetyl-D-phenylalanine as the starting substance. After the consumption of 1.0 mole of ketene, 90% of the N-acetyl D-phenylalanine is racemized, and after the consumption of 1.18 moles of ketene, 95% of the N-acetyl D-phenylalanine is racemized.

EXAMPLE 7

Ketene is introduced at 70° C. into an aqueous solution of one mole of N-acetyl-L-phenylalanine sodium salt, as in Example 1 but containing 0.2 mole of acetic acid. After the consumption of 0.9 mole of ketene, 90% of the N-acetyl-L-phenylalanine is racemized; after the consumption of 1.06 moles of ketene, 95% of the N-acetyl-L-phenylalanine is racemized.

EXAMPLE 8

Into an aqueous solution of 1 mole of N-acetyl-L-phenylalanine sodium salt in which the N-acetyl-L-phenylalanine content is 10 wt-%, and 0.2 mole of acetic acid, ketene is introduced at 70° C. After the consumption of 2.2 moles of ketene, 90% of the N-acetyl-L-phenylalanine is racemized.

EXAMPLE 9

Using the procedure of Example 8, but with the N-acetyl-L-phenylalanine content 30 wt-%: after the consumption of 0.62 mole of ketene, 90% of the N-acetyl-L-phenylalanine is racemized; after consumption of 0.7 mole of ketene, 95% of the N-acetyl-L-phenylalanine is racemized.

EXAMPLE 10

Using the procedure of 8, but with the N-acetyl-L-phenylalanine content 40 wt.-%: after consumption of 0.65 mole of ketene, 90% of the N-acetyl-L-phenylalanine is racemized.

EXAMPLE 11

Ketene is introduced at 80° C. into an aqueous solution of one mole of N-acetyl-D-phenylglycine sodium salt and 0.2 mole of acetic acid, in which the N-acetyl-D-phenylglycine content is 30 wt.-%. After the consumption of 1.1 mole of ketene, 90% of the N-acetyl-D-phenylglycine is racemized.

EXAMPLE 12

Ketene is introduced at 80° C. into an aqueous solution of one mole of N-acetyl-L-alanine sodium salt and 0.2 mole of acetic acid, in which the N-acetyl-L-alanine content is 20% by weight. After the consumption of 1.8 mole of ketene, 90% of the N-acetyl-L-alanine is racemized.

EXAMPLE 13

Ketene is introduced at 70° C. into an aqueous solution of one mole of N-acetyl-L-serine sodium salt and 0.2 mole of acetic acid, in which the N-acetyl-L-serine content is 25 wt.-%. After the consumption of 2.0 moles of ketene, 90% of the N-acetyl-L-serine has been racemized, without the formation of any O-acetyl serine.

EXAMPLE 14

Ketene is introduced at 80° C. into an aqueous solution of 1 mole of N-α-acetyl-L-tryptophan sodium salt and 0.2 mole of acetic acid, the N-α-acetyl-L-tryptophan content being 30 wt.-%. After the consumption of 1.1 mole of ketene, 90% of the N-α-acetyl-L-tryptophan is racemized. No acetylation takes place on the indole ring.

EXAMPLE 15

Ketene is introduced at 70° C. into an aqueous solution of 0.6 mole of N-acetyl-L-methionine sodium salt and 0.12 mole of acetic acid, in which the N-acetyl-L-methionine content is 25 wt.-%. After the consumption of 0.6 mole of ketene, 93% of the N-acetyl-L-methionine is racemized.

What is claimed is:

1. Method for the racemization of optically active N-acyl amino acids in aqueous solution, which comprises reacting an aqueous solution of an alkali metal salt of an optically active N-acyl amino acid with ketene at a temperature between 0° C. and the boiling point of the solution.

2. Method of claim 1 wherein the racemization reaction with ketene takes place at a temperature between 30° and 90° C.

3. Method of claim 1, wherein the pH of the solution is between pH 2 and pH 11.

4. Method of claim 3, wherein the pH is between pH 3 and pH 9.

5. Method of claim 3 wherein the pH is between pH 4 and pH 7.

6. Method of claim 4, wherein an acid is added for the adjustment of the pH value.

7. Method of claim 6 wherein the acid which is added is acetic acid.

8. Method of claim 1 wherein an alkali metal salt of an N-acetyl amino acid is racemized in a 10 to 50 wt-% aqueous solution, with respect to the acetyl-amino acid.

9. Method of claim 8 wherein an alkali metal salt of an N-acetyl amino acid is racemized in an approximately 20 to 35 wt.-% aqueous solution, with respect to the acetylamino acid.

* * * * *